(12) United States Patent
Woo et al.

(10) Patent No.: US 7,833,926 B2
(45) Date of Patent: *Nov. 16, 2010

(54) ARYLPHENOXY CATALYST SYSTEM FOR PRODUCING ETHYLENE HOMOPOLYMER OR COPOLYMERS OF ETHYLENE AND α-OLEFINS

(75) Inventors: Tae Woo Woo, Daejeon (KR); Myung Ahn Ok, Daejeon (KR); Jong Sok Hahn, Daejeon (KR); Mal-Ou Lee, Daejeon (KR); Sang Ook Kang, Seoul (KR); Sung-bo Ko, Daejeon (KR); Tae-Jin Kim, Daejeon (KR); Sung-Kwan Kim, Gyeongsangnam-do (KR)

(73) Assignee: SK Energy Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,816

(22) Filed: Jul. 31, 2009

(65) Prior Publication Data

US 2009/0326175 A1 Dec. 31, 2009

Related U.S. Application Data

(62) Division of application No. 11/280,930, filed on Nov. 15, 2005, now abandoned.

(30) Foreign Application Priority Data

Jul. 1, 2005 (KR) .................. 10-2005-0059354

(51) Int. Cl.
*C08F 4/64* (2006.01)
*C08F 4/6592* (2006.01)
*C07J 17/00* (2006.01)
*B01J 31/22* (2006.01)

(52) U.S. Cl. ............ 502/152; 502/103; 526/160; 526/172; 556/53

(58) Field of Classification Search ............... 502/103, 502/152; 526/133, 160, 161, 165, 348, 943
See application file for complete search history.

(56) References Cited

U.S. PATENT DOCUMENTS 4,752,597 A 6/1988 Turner 5,079,205 A 1/1992 Canich
5,198,401 A 3/1993 Turner et al.
6,329,478 B1 12/2001 Katayama et al.

FOREIGN PATENT DOCUMENTS

| EP | 0 320 762 B1 | 6/1989 |
|---|---|---|
| EP | 0 372 632 B1 | 6/1990 |
| EP | 0 416 815 B1 | 3/1991 |
| EP | 0 420 436 B1 | 4/1991 |
| EP | 0 842 939 B1 | 5/1998 |
| JP | 2-84405 A | 3/1990 |
| JP | 3-2347 A | 1/1991 |
| KR | 2001-0074722 A | 8/2001 |

OTHER PUBLICATIONS

Patent Abstracts of Japan for 63-92621 published on Apr. 23, 1988.
Kotohiro Nomura, et al., Synthesis of Various Nonbridged Titanium(IV) Cyclopentadienyl-Aryloxy Complexes of the Type CpTi(OAr)X$_2$ and Their Use in the Catalysis of Alkene Polymerization. Important Roles of Substituents on both Aryloxy and Cyclopentadienyl Groups, *Organometallics* 1998, 17, pp. 2152-2154.
Matthew G. Thorn, et al., Cationic Group 4 metal alkyl compounds containing aryloxide ligation: synthesis, structure, reactivity and polymerization studies, Journal of Organometallic Chemistry 591 (1999) pp. 148-162.

*Primary Examiner*—Caixia Lu
(74) *Attorney, Agent, or Firm*—McDermott Will & Emery LLP

(57) ABSTRACT

The present invention relates to an arylphenoxy catalyst system producing an ethylene homopolymer or copolymers of ethylene and α-olefins, and a method of producing an ethylene homopolymer or copolymers of ethylene and α-olefins having a high molecular weight under a high temperature solution polymerization condition using the same. The catalyst system includes a group IV arylphenoxy-based transition metal catalyst and an aluminoxane cocatalyst or a boron compound cocatalyst. In the transition metal catalyst, a cyclopentadiene derivative and arylphenoxide as fixed ligands are located around the group IV transition metal, arylphenoxide is substituted with at least one aryl derivative and is located at the ortho position thereof, and the ligands are not crosslinked to each other. The catalyst includes an environmentally-friendly raw material, synthesis of the catalyst is economical, and thermal stability of the catalyst is excellent. It is useful for producing an ethylene homopolymer or copolymers of ethylene and α-olefins having various physical properties in commercial polymerization processes.

7 Claims, 2 Drawing Sheets monoclinic, *P*2₁/*c*, R1 = 0.0498

Orthorhombic, (Pna21), R1 = 0.0430

ARYLPHENOXY CATALYST SYSTEM FOR PRODUCING ETHYLENE HOMOPOLYMER OR COPOLYMERS OF ETHYLENE AND α-OLEFINS

INCORPORATION BY REFERENCE

The present application is a divisional of U.S. patent application Ser. No. 11/280,930, filed Nov. 15, 2005, which claims priority under 35 U.S.C. §119 to Korean Patent Application No. 10-2005-0059354 filed on Jul. 1, 2005. The content of each application is incorporated herein by reference in their entireties.

BACKGROUND OF THE INVENTION

1. Field of the Invention

The present invention relates to an arylphenoxy catalyst system for producing ethylene homopolymer or copolymers of ethylene and α-olefins. More particularly, the present invention pertains to a group IV transition metal catalyst expressed by Formula 1, a catalyst system which includes the arylphenoxy-based transition metal catalyst and an aluminoxane cocatalyst or a boron compound cocatalyst, and a method of producing an ethylene homopolymer or copolymers of ethylene and α-olefins using the same. In the transition metal catalyst, a cyclopentadiene derivative and an arylphenoxide as fixed ligands are located around a group IV transition metal, arylphenoxide ligand is substituted with at least one aryl derivative and is located at ortho position thereof, and the ligands are not crosslinked to each other.

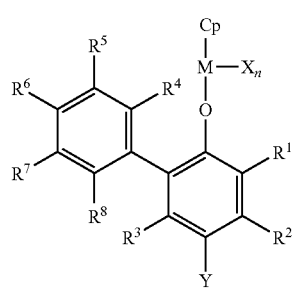

Formula 1

In Formula 1, wherein M is the group IV transition metal of the periodic table;

Cp is cyclopentadienyl group capable of forming an $\eta^5$-bond along with the central metal, or derivatives thereof;

$R^1$, $R^2$, $R^3$, $R^4$, $R^5$, $R^6$, $R^7$, and $R^8$ of the arylphenoxide ligand are independently a hydrogen atom, a halogen atom, a $C_1$-$C_{20}$ linear or nonlinear alkyl group arbitrarily substituted with one or more halogen atoms, a silyl group which contains the $C_1$-$C_{20}$ linear or nonlinear alkyl group arbitrarily substituted with one or more halogen atoms, a $C_6$-$C_{30}$ aryl group arbitrarily substituted with one or more halogen atoms, a $C_7$-$C_{30}$ arylalkyl group arbitrarily substituted with one or more halogen atoms, an alkoxy group which contains the $C_1$-$C_{20}$ alkyl group arbitrarily substituted with one or more halogen atoms, or a $C_3$-$C_{20}$ alkyl-substituted or $C_6$-$C_{20}$ aryl-substituted siloxy group, where the substituent groups may be arbitrarily bonded to form rings;

X can be independently selected from a group including the halogen atom, the $C_1$-$C_{20}$ alkyl group which is not a Cp derivative, the $C_7$-$C_{30}$ arylalkyl group, an alkoxy group which contains the $C_1$-$C_{20}$ alkyl group, the $C_3$-$C_{20}$ alkyl-substituted siloxy group, and an amido group which has a $C_1$-$C_{20}$ hydrocarbon group;

Y is the hydrogen atom, the halogen atom, the $C_1$-$C_{20}$ linear or nonlinear alkyl group arbitrarily substituted with one or more halogen atoms, the silyl group which contains the $C_1$-$C_{20}$ linear or nonlinear alkyl group arbitrarily substituted with one or more halogen atoms, the $C_6$-$C_{30}$ aryl group arbitrarily substituted with one or more halogen atoms, the $C_7$-$C_{30}$ arylalkyl group arbitrarily substituted with one or more halogen atoms, the alkoxy group which contains the $C_1$-$C_{20}$ alkyl group arbitrarily substituted with one or more halogen atoms, the $C_3$-$C_{20}$ alkyl-substituted or $C_6$-$C_{20}$ aryl-substituted siloxy group, the amido group or a phosphido group which contains the $C_1$-$C_{20}$ hydrocarbon group, or a $C_1$-$C_{20}$ alkyl-substituted mercapto or nitro group; and n is 1 or 2 depending on the oxidation state of the transition metal.

2. Description of the Related Art

Conventionally, Ziegler-Natta catalyst system which includes a main catalyst component of titanium or vanadium compounds and a cocatalyst component of alkyl aluminum compounds has been used to produce an ethylene homopolymer or copolymers of ethylene and α-olefins. However, the Ziegler-Natta catalyst system is disadvantageous in that, even though it is highly active in the polymerization of ethylene, the molecular weight distribution of a resultant polymer is wide, and particularly, a compositional distribution is non-uniform in the copolymer of ethylene and α-olefin due to heterogeneous catalyst active sites.

Recently, the metallocene catalyst system which comprises a metallocene compound of a group IV transition metal in the periodic table, such as titanium, zirconium, or hafnium, and methylaluminoxane as a cocatalyst has been developed. Since the metallocene catalyst system is a homogeneous catalyst having one kind of catalytic active site, it can be used to produce polyethylene having a narrow molecular weight distribution and a uniform compositional distribution in comparison with the conventional Ziegler-Natta catalyst system. For example, EP Pat. Nos. 320762 and 372632, and Japanese Patent Laid-Open Publication Nos. Sho. 63-092621, Hei. 02-84405, and Hei. 03-2347 disclose metallocene compounds, such as $Cp_2TiCl_2$, $Cp_2ZrCl_2$, $Cp_2ZrMeCl$, $Cp_2ZrMe_2$, or (ethylene-bis tetrahydroindenyl)$ZrCl_2$, activated with methylaluminoxane as a cocatalyst to polymerize ethylene at high catalytic activity, thereby making it possible to produce polyethylene having a molecular weight distribution (Mw/Mn) of 1.5-2.0. However, it is difficult to produce a polymer having a high molecular weight using the above catalyst system. Particularly, if it is applied to a solution polymerization process which is conducted at high temperatures of 140° C. or higher, polymerization activity is rapidly reduced and a β-hydrogen elimination reaction is dominant, thus it is unsuitable for producing a high molecular weight polymer having a weight average molecular weight (Mw) of 100,000 or more.

Meanwhile, a constrained geometry non-metallocene catalyst (a so-called single-site catalyst) in which a transition metal is connected to a ligand system in a ring shape has been suggested as a catalyst which has high catalytic activity and is capable of producing a polymer having a high molecular weight in polymerization of only ethylene or in copolymerization of ethylene and α-olefin under a solution polymerization condition. EP Pat. Nos. 0416815 and 0420436 suggest a catalytic system in which a transition metal is connected to cyclopentadiene ligand and an amide group in a ring shape, and EP Pat. No. 0842939 discloses a catalyst in which a phenol-based ligand as an electron donor compound is connected with a cyclopentadiene ligand in a ring shape. However, since the cyclization of the ligands along with the transition metal compound is achieved at very low yield during synthesis of the constrained geometry catalyst, it is difficult to commercialize them.

Meanwhile, an example of non-metallocene catalysts which is not a constrained geometry catalyst and is capable of being used under a high temperature solution condition are disclosed in U.S. Pat. No. 6,329,478 and Korean Patent Laid-Open Publication No. 2001-0074722. The patents disclose a single-site catalyst using one or more phosphinimine compounds as a ligand, having high ethylene conversion during copolymerization of ethylene and α-olefins under the high temperature solution polymerization condition at 140° C. or higher. However, a limited range of phosphine compounds may be used to produce the phosphinimine ligand, and, since these compounds are harmful to the environment and to humans, it might have some difficulties in using them to produce general-purpose olefin polymers. U.S. Pat. No. 5,079,205 discloses a catalyst having a bis-phenoxide ligand, but it has too low catalytic activity to be commercially used.

In addition to the above-mentioned examples, Nomura et al., *Organometallics* 1998, 17, 2152 discloses the synthesis of a non-metallocene catalyst with a phenol-based ligand and polymerization using the same, in which the substituents on the phenol ligand are limited to only simple alkyl substituents such as isopropyl group. On the other hand, Rothwell, P. et al., *J. Organomet. Chem.* 1999, 591, 148 discloses an arylphenoxy ligand, but does not suggest the effects of aryl substituent at the ortho-position.

SUMMARY OF THE INVENTION

To overcome the above problems occurring in the prior art, the present inventors have conducted extensive studies, resulting in the finding that a non-bridged type transition metal catalyst, in which cyclopentadiene derivatives and arylphenoxide substituted with at least one aryl derivative at the ortho-position thereof are used as fixed ligands, shows an excellent thermal stability. Based on the above finding, a catalyst, which is used to produce an ethylene homopolymer or copolymers of ethylene and α-olefins having a high molecular weight, at a high activity during a solution polymerization process at high temperatures of 80° C. or higher, has been developed, thereby the present invention is accomplished.

Accordingly, an object of the present invention is to provide a single-site catalyst and a high temperature solution polymerization method using the same. The single-site catalyst includes environmentally-friendly raw materials, synthesis of the catalyst is very economical and thermal stability of the catalyst is excellent. In the solution polymerization method, it is possible to easily and commercially produce an ethylene homopolymer or copolymers of ethylene and α-olefins having various physical properties using the catalyst.

In order to accomplish the above object, an aspect of the present invention provides an arylphenoxy-based transition metal catalyst expressed by Formula 1, which includes a cyclopentadiene derivative and arylphenoxide as fixed ligands around a transition metal. Arylphenoxide is substituted with at least one aryl derivative and is located at the ortho position thereof, and the ligands are not crosslinked to each other.

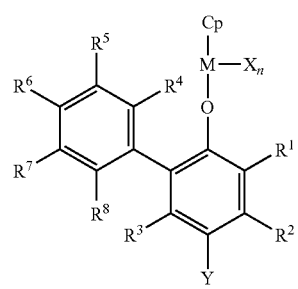

Formula 1

In Formula 1, wherein M is the group IV transition metal of a periodic table;

Cp is cyclopentadienyl group, capable of forming an $\eta^5$-bond along with the central metal, or a derivative thereof;

$R^1$, $R^2$, $R^3$, $R^4$, $R^5$, $R^6$, $R^7$, and $R^8$ of the arylphenoxide ligand are independently a hydrogen atom, a halogen atom, a $C_1$-$C_{20}$ linear or nonlinear alkyl group arbitrarily substituted with one or more halogen atoms, a silyl group which contains the $C_1$-$C_{20}$ linear or nonlinear alkyl group arbitrarily substituted with one or more halogen atoms, a $C_6$-$C_{30}$ aryl group arbitrarily substituted with one or more halogen atoms, a $C_7$-$C_{30}$ arylalkyl group arbitrarily substituted with one or more halogen atoms, an alkoxy group which has the $C_1$-$C_{20}$ alkyl group arbitrarily substituted with one or more halogen atoms, or a $C_3$-$C_{20}$ alkyl-substituted or $C_6$-$C_{20}$ aryl-substituted siloxy group, optionally with the proviso that the substituent groups may be arbitrarily bonded to form rings;

X can include the halogen atom, the $C_1$-$C_{20}$ alkyl group which is not a Cp derivative, the $C_7$-$C_{30}$ arylalkyl group, an alkoxy group which contains the $C_1$-$C_{20}$ alkyl group, the $C_3$-$C_{20}$ alkyl-substituted siloxy group, and an amido group which contains a $C_1$-$C_{20}$ hydrocarbon group;

Y is the hydrogen atom, the halogen atom, the $C_1$-$C_{20}$ linear or nonlinear alkyl group arbitrarily substituted with one or more halogen atoms, the silyl group which contains the $C_1$-$C_{20}$ linear or nonlinear alkyl group arbitrarily substituted with one or more halogen atoms, the $C_6$-$C_{30}$ aryl group arbitrarily substituted with one or more halogen atoms, the $C_7$-$C_{30}$ arylalkyl group arbitrarily substituted with one or more halogen atoms, the alkoxy group which has the $C_1$-$C_{20}$ alkyl group arbitrarily substituted with one or more halogen atoms, the $C_3$-$C_{20}$ alkyl-substituted or $C_6$-$C_{20}$ aryl-substituted siloxy group, the amido group or a phosphido group which has the $C_1$-$C_{20}$ hydrocarbon group, or a $C_1$-$C_{20}$ alkyl-substituted mercapto or nitro group; and n is 1 or 2 depending on the oxidation state of the transition metal.

Another aspect of the present invention relates to a catalyst system which includes the transition metal catalyst, and aluminum or a boron compound as a cocatalyst.

Still another aspect of the present invention relates to a method of producing ethylene polymers using the transition metal catalyst.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
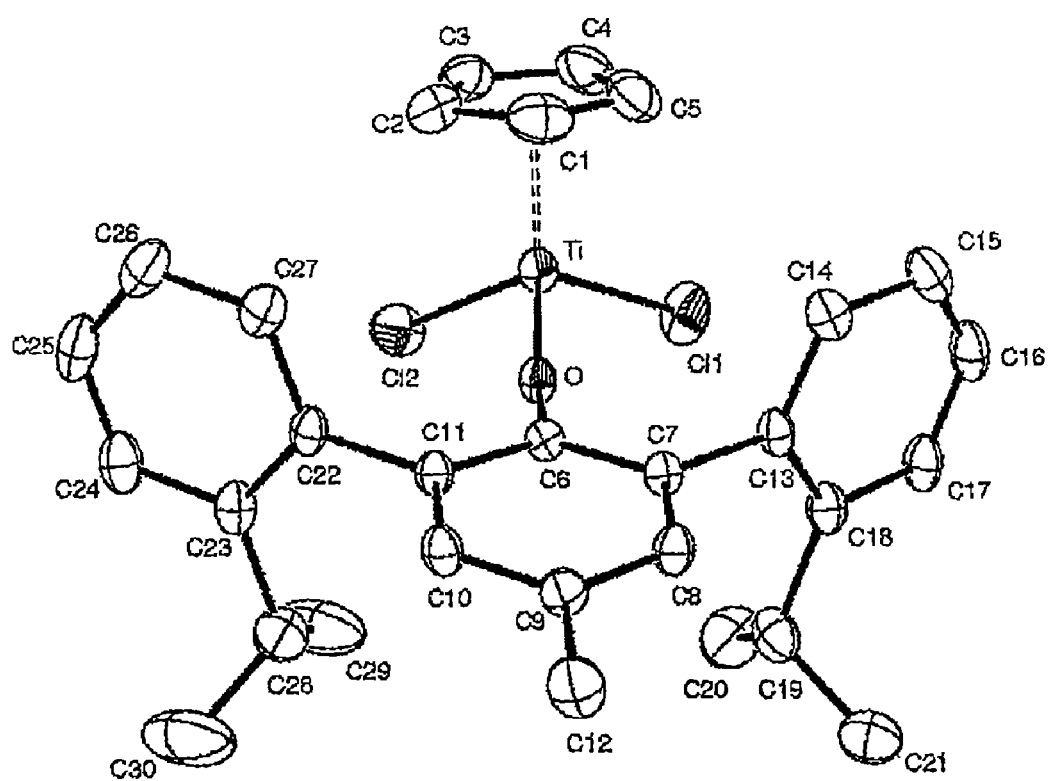
FIG. 1 illustrates a crystalline structure of a (dichloro)(cyclopentadienyl)(4-methyl-2,6-bis(2'-isopropylphenyl)phenoxy)titanium(IV) catalyst according to an embodiment of the present invention.
Figure 2:
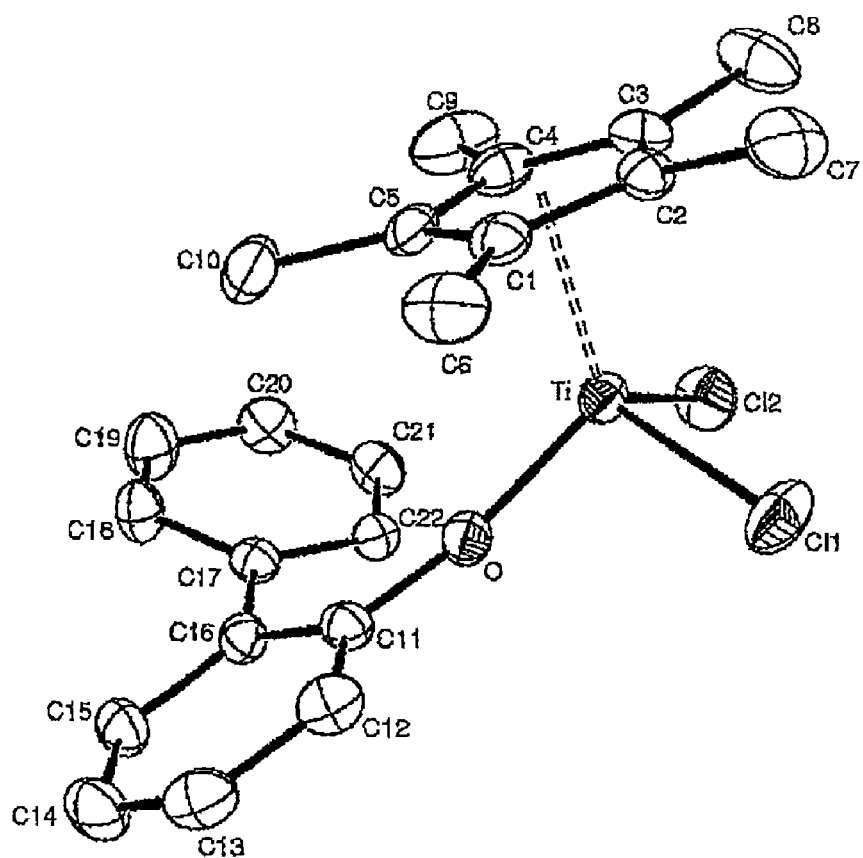
FIG. 2 illustrates a crystalline structure of a (dichloro)(pentamethylcyclopentadienyl) (2-phenylphenoxy)titanium(IV) catalyst according to another embodiment of the present invention.

Hereinafter, a detailed description will be given of the present invention.

M of the transition metal catalyst in Formula 1 is preferably titanium, zirconium, or hafnium. Furthermore, Cp is a cyclopentadiene anion capable of forming an $\eta^5$-bond along with a central metal, or a derivative thereof. In detail, it is exemplified by cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, and isopropylfluorenyl.

With respect to $R^1$, $R^2$, $R^3$, $R^4$, $R^5$, $R^6$, $R^7$, and $R^8$ of an arylphenoxide ligand, a halogen atom is exemplified by fluorine, chlorine, bromine, and iodine atoms; and a $C_1$-$C_{20}$ alkyl group is exemplified by methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, and n-eicosyl group, and preferably, methyl group, ethyl group, isopropyl group, tert-butyl group, and amyl group. The alkyl group may arbitrarily be substituted with one or more halogen atoms, and is exemplified by fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, or perbromoeicosyl group. Among them, trifluoromethyl group is preferable. In $R^1$, $R^2$, $R^3$, $R^4$, $R^5$, $R^6$, $R^7$, and $R^8$, a $C_1$-$C_{20}$ alkyl-substituted silyl group is exemplified by methylsilyl group, ethylsilyl group, phenylsilyl group, dimethylsilyl group, diethylsilyl group, diphenylsilyl group, trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyldimethylsilyl group, tri-n-pentylsilyl group, tri-n-hexylsilyl group, tricyclohexylsilyl group, or triphenylsilyl group, and preferably trimethylsilyl group, tert-butyldimethylsilyl group, and triphenylsilyl group. A $C_6$-$C_{30}$ aryl group is exemplified by phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, biphenyl group, fluorenyl group, triphenyl group, naphthyl group, or anthracenyl group, and preferably, phenyl group, naphthyl group, biphenyl group, 2-isopropylphenyl group, 3,5-xylyl group, and 2,4,6-trimethylphenyl group. A $C_7$-$C_{30}$ arylalkyl group is exemplified by benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, or anthracenylmethyl group, and preferably, benzyl group. A $C_1$-$C_{20}$ alkoxy group is exemplified by methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, or n-eicosoxy group, and preferably, methoxy group, ethoxy group, isopropoxy group, and tert-butoxy group. A $C_3$-$C_{20}$ alkyl-substituted or $C_6$-$C_{20}$ aryl-substituted siloxy group is exemplified by trimethylsiloxy group, triethylsiloxy group, tri-n-propylsiloxy group, triisopropylsiloxy group, tri-n-butylsiloxy group, tri-sec-butylsiloxy group, tri-tert-butylsiloxy group, tri-isobutylsiloxy group, tert-butyldimethylsiloxy group, tri-n-pentylsiloxy group, tri-n-hexylsiloxy group, tricyclohexylsiloxy group, or triphenylsiloxy group, and preferably, trimethylsiloxy group, tert-butyldimethylsiloxy group, and triphenylsiloxy group. The above-mentioned substituent groups may be arbitrarily substituted with one or more halogen atoms.

In X, a halogen atom is exemplified by fluorine, chlorine, bromine, and iodine atoms and a $C_1$-$C_{20}$ alkyl group which is not the Cp derivative is exemplified by methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, and n-eicosyl group, and preferably, methyl group, ethyl group, isopropyl group, tert-butyl group, and amyl group. A $C_7$-$C_{30}$ arylalkyl group is exemplified by benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, or anthracenylmethyl group, and preferably, benzyl group. A $C_1$-$C_{20}$ alkoxy group is exemplified by methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, or n-eicosoxy group, and preferably, methoxy group, ethoxy group, isopropoxy group, and tert-butoxy group. A $C_3$-$C_{20}$ alkyl-substituted siloxy group is exemplified by trimethylsiloxy group, triethylsiloxy group, tri-n-propylsiloxy group, triisopropylsiloxy group, tri-n-butylsiloxy group, tri-sec-butylsiloxy group, tri-tert-butylsiloxy group, tri-isobutylsiloxy group, tert-butyldimethylsiloxy group, tri-n-pentylsiloxy group, tri-n-hexylsiloxy group, or tricyclohexylsiloxy group, and preferably, trimethylsiloxy group and tert-butyldimethylsiloxy group.

An amido group or a phosphido group having a $C_1$-$C_{20}$ hydrocarbon group is exemplified by dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, dibenzylamide group, methylethylamide group, methylphenylamide group, benzylhexylamide group, bistrimethylsilylamino group, or bis-tert-butyldimethylsilylamino group, or phosphido group which is substituted with the same alkyl. Among them, dimethylamino group, diethylamino group, and diphenylamide group are preferable.

In Y, a halogen atom is exemplified by fluorine, chlorine, bromine, and iodine atom; and a $C_1$-$C_{20}$ alkyl group is exemplified by methyl group, ethyl group, n-propyl group, isopropyl group, n-butyl group, sec-butyl group, tert-butyl group, n-pentyl group, neopentyl group, amyl group, n-hexyl group, n-octyl group, n-decyl group, n-dodecyl group, n-pentadecyl group, and n-eicosyl group, and preferably, methyl group, ethyl group, isopropyl group, tert-butyl group, and amyl group. The $C_1$-$C_{20}$ alkyl group which is arbitrarily substituted with one or more halogen atoms is exemplified by fluoromethyl group, difluoromethyl group, trifluoromethyl group, chloromethyl group, dichloromethyl group, trichloromethyl group, bromomethyl group, dibromomethyl group, tribromomethyl group, iodomethyl group, diiodomethyl group, triiodomethyl group, fluoroethyl group, difluoroethyl group, trifluoroethyl group, tetrafluoroethyl group, pentafluoroethyl group, chloroethyl group, dichloroethyl group, trichloroethyl group, tetrachloroethyl group, pentachloroethyl group, bromoethyl group, dibromoethyl group, tribromoethyl group, tetrabromoethyl group, pentabromoethyl group, perfluoropropyl group, perfluorobutyl group, perfluoropentyl group, perfluorohexyl group, perfluorooctyl group, perfluorododecyl group, perfluoropentadecyl group, perfluoroeicosyl group, perchloropropyl group, perchlorobutyl group, perchloropentyl group, perchlorohexyl group, perchlorooctyl group, perchlorododecyl group, perchloropentadecyl group, perchloroeicosyl group, perbromopropyl group, perbromobutyl group, perbromopentyl group, perbromohexyl group, perbromooctyl group, perbromododecyl group, perbromopentadecyl group, or perbromoeicosyl group, and preferably, trifluoromethyl group. Furthermore, in Y, a $C_1$-$C_{20}$ alkyl-substituted silyl group is exemplified by methylsilyl group, ethylsilyl group, phenylsilyl group, dimethylsilyl group, diethylsilyl group, diphenylsilyl group, trimethylsilyl group, triethylsilyl group, tri-n-propylsilyl group, triisopropylsilyl group, tri-n-butylsilyl group, tri-sec-butylsilyl group, tri-tert-butylsilyl group, tri-isobutylsilyl group, tert-butyldimethylsilyl group, tri-n-pentylsilyl group, tri-n-hexylsilyl group, tricyclohexylsilyl group, or triphenylsilyl group, and preferably trimethylsilyl group, tert-butyldimethylsilyl group, and triphenylsilyl group. A $C_6$-$C_{30}$ aryl group is exemplified by phenyl group, 2-tolyl group, 3-tolyl group, 4-tolyl group, 2,3-xylyl group, 2,4-xylyl group, 2,5-xylyl group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, biphenyl group, fluorenyl group, triphenyl group, naphthyl group, or anthracenyl group, and preferably, phenyl group, naphthyl group, biphenyl group, 2-isopropylphenyl group, 3,5-xylyl group, and 2,4,6-trimethylphenyl group. A $C_7$-$C_{30}$ arylalkyl group is exemplified by benzyl group, (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (4,6-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (n-tetradecylphenyl)methyl group, naphthylmethyl group, or anthracenylmethyl group, and preferably, benzyl group. A $C_1$-$C_{20}$ alkoxy group is exemplified by methoxy group, ethoxy group, n-propoxy group, isopropoxy group, n-butoxy group, sec-butoxy group, tert-butoxy group, n-pentoxy group, neopentoxy group, n-hexoxy group, n-octoxy group, n-dodecoxy group, n-pentadecoxy group, or n-eicosoxy group, and preferably, methoxy group, ethoxy group, isopropoxy group, and tert-butoxy group. A $C_3$-$C_{20}$ alkyl-substituted or $C_6$-$C_{20}$ aryl-substituted siloxy group is exemplified by trimethylsiloxy group, triethylsiloxy group, tri-n-propylsiloxy group, triisopropylsiloxy group, tri-n-butylsiloxy group, tri-sec-butylsiloxy group, tri-tert-butylsiloxy group, tri-isobutylsiloxy group, tert-butyldimethylsiloxy group, tri-n-pentylsiloxy group, tri-n-hexylsiloxy group, tricyclohexylsiloxy group, or triphenylsiloxy group, and preferably, trimethylsiloxy group, tert-butyldimethylsiloxy group, and triphenylsiloxy group. The above-mentioned substituent groups may be substituted with one or more halogen atoms. As well, with respect to Y, an amido group or a phosphido group having a $C_1$-$C_{20}$ hydrocarbon group is exemplified by dimethylamino group, diethylamino group, di-n-propylamino group, diisopropylamino group, di-n-butylamino group, di-sec-butylamino group, di-tert-butylamino group, diisobutylamino group, tert-butylisopropylamino group, di-n-hexylamino group, di-n-octylamino group, di-n-decylamino group, diphenylamino group, dibenzylamide group, methylethylamide group, methylphenylamide group, benzylhexylamide group, bistrimethylsilylamino group, or bis-tert-butyldimethylsilylamino group, or phosphido group which is substituted with the same alkyl. Among them, dimethylamino group, diethylamino group, and diphenylamide group are preferable. A $C_1$-$C_{20}$ mercapto group is exemplified by methyl mercaptan, ethyl mercaptan, propyl mercaptan, isopropyl mercaptan, 1-butyl mercaptan, or isopentyl mercaptan, and preferably, ethyl mercaptan and isopropyl mercaptan.

In a representative process of synthesizing the transition metal complex of Formula 1, a substituted or unsubstituted arylphenoxide-based ligand is produced and reacted with a group IV transition metal compound having one cyclopentadiene derivative. To produce a substituted or unsubstituted arylphenol-based ligand, an anisole compound, which is expressed by Formula 2 and substituted with one or two halogen atoms, and a substituted or unsubstituted arylboronic acid, which is as shown in Formula 3, are reacted with an organic phosphine ligand using a palladium metal compound as a catalyst in an organic solvent at preferably −20 to 120° C. to produce an aryl-substituted anisole compound, and reacted with a tribromoboron compound in an organic solvent at a temperature preferably ranging from −78 to 50° C. to produce an aryl-substituted phenoxide ligand. The ligand thus produced is reacted with sodium hydride, alkyl lithium, or alkyl magnesium halide compound in an organic solvent at a temperature preferably ranging from −78 to 120° C. so as to be converted into anions, and then subjected to a ligand exchange reaction along with the group IV transition metal compound which is expressed by Formula 4 and has one cyclopentadiene derivative at −20 to 120° C. in an equivalent ratio. The resulting product is purified to produce an arylphenoxide-based transition metal catalyst component.

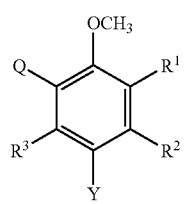

Formula 2

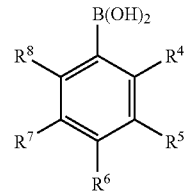

Formula 3

In the above Formula 2 or 3, $R^1$, $R^2$, $R^3$, $R^4$, $R^5$, $R^6$, $R^7$, and $R^8$ are independently a hydrogen atom, a halogen atom, a $C_1$-$C_{20}$ linear or nonlinear alkyl group arbitrarily substituted with one or more halogen atoms, a silyl group which contains the $C_1$-$C_{20}$ linear or nonlinear alkyl group arbitrarily substituted with one or more halogen atoms, a $C_6$-$C_{30}$ aryl group arbitrarily substituted with one or more halogen atoms, a $C_7$-$C_{30}$ arylalkyl group arbitrarily substituted with one or more halogen atoms, a $C_1$-$C_{20}$ alkylalkoxy group arbitrarily substituted with one or more halogen atoms, or a $C_3$-$C_{20}$ alkyl-substituted siloxy group or $C_6$-$C_{20}$ aryl-substituted siloxy group, optionally with the proviso that the substituent groups may be arbitrarily bonded to form rings; Q is the halogen atom; and Y is the hydrogen atom, the halogen atom, the $C_1$-$C_{20}$ linear or nonlinear alkyl group arbitrarily substituted with one or more halogen atoms, the silyl group which contains the $C_1$-$C_{20}$ linear or nonlinear alkyl group arbitrarily substituted with one or more halogen atoms, the $C_6$-$C_{30}$ aryl group arbitrarily substituted with one or more halogen atoms, the $C_7$-$C_{30}$ arylalkyl group arbitrarily substituted with one or more halogen atoms, the $C_1$-$C_{20}$ alkylalkoxy group arbitrarily substituted with one or more halogen atoms, the $C_3$-$C_{20}$ alkyl-substituted siloxy group or $C_6$-$C_{20}$ aryl-substituted siloxy group, the amido group or a phosphido group which has the $C_1$-$C_{20}$ hydrocarbon group, or a $C_1$-$C_{20}$ alkyl-substituted mercapto or nitro group.

$$CpM(X)_m \qquad \text{Formula 4}$$

In Formula 4, Cp is cyclopentadienyl capable of forming an $\eta^5$-bond along with a central metal, or a derivative thereof, M is a group IV transition metal in a periodic table, X is a halogen atom, a $C_1$-$C_{20}$ alkyl group which is not a Cp derivative, a $C_7$-$C_{30}$ arylalkyl group, a $C_1$-$C_{20}$ alkylalkoxy group, a $C_3$-$C_{20}$ alkyl-substituted siloxy group, or an amido group having a $C_1$-$C_{20}$ hydrocarbon group, and m is 2 or 3 depending on the oxidation state of the transition metal.

Meanwhile, in order to use the transition metal catalyst of Formula 1 as an active catalyst component which is used to produce an ethylene homopolymer or copolymer of ethylene and an α-olefin comonomers, an X ligand is extracted from a transition metal complex to convert the central metal into cations, and aluminoxane compounds or boron compounds which are capable of acting as opposite ions having weak bonding strength, that is, anions, are used along with a cocatalyst.

As well known in the art, aluminoxane, which is expressed by the following Formula 5 or 6, is frequently used as the aluminoxane compound used in the present invention.

$$(-Al(R^9)-O-)_m \qquad \text{Formula 5}$$

$$(R^9)_2Al-(-O(R^9)-)_p-(R^9)_2 \qquad \text{Formula 6}$$

In the above Formula, $R^9$ is a $C_1$-$C_{20}$ alkyl group, and preferably, a methyl group or an isobutyl group, and m and p are integers ranging from 5 to 20.

In order to use the transition metal catalyst of the present invention as an active catalyst, the mixing ratio of the two components is set so that the molar ratio of the central metal to aluminum is preferably 1:20 to 1:10,000, and more preferably, 1:50 to 1:5,000.

Furthermore, a boron compound which is capable of being used as a cocatalyst of the present invention may be selected from compounds of the following Formula 7 to 9 as disclosed in U.S. Pat. No. 5,198,401.

$$B(R^{10})_3 \qquad \text{Formula 7}$$

$$[R^{11}]^+[B(R^{10})_4]^- \qquad \text{Formula 8}$$

$$[(R^{12})_qZH]^+[B(R^{10})_4]^- \qquad \text{Formula 9}$$

In the above Formulae, B is a boron atom; $R^{10}$ is an unsubstituted phenyl group, or a phenyl group which is substituted with 3 to 5 substituent groups selected from the group consisting of a $C_1$-$C_4$ alkyl group which is substituted or unsubstituted with a fluorine atom and a $C_1$-$C_4$ alkoxy group which is substituted or unsubstituted with the fluorine atom; $R^{11}$ is a $C_5$-$C_7$ cyclic aromatic cation or an alkyl-substituted aromatic cation, for example, triphenylmethyl cation; Z is a nitrogen atom or a phosphorus atom; $R^{12}$ is a $C_1$-$C_4$ alkyl radical or an anilinium radical which is substituted with two $C_1$-$C_4$ alkyl groups along with a nitrogen atom; and q is an integer of 2 or 3.

Examples of the boron-based cocatalyst include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate, and tetrakis(3,5-bistrifluoromethylphenyl)borate. Furthermore, a combination of the above-mentioned examples is exemplified by ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, or tri(dimethylphenyl)phosphonium tetrakis(pentafluorophenyl)borate, and preferably, N,N-dimethylanilinium tetrakis(pentafluorophenyl)borate, triphenylmethylinium tetrakis(pentafluorophenyl)borate, and tris(pentafluoro)borane.

In a catalyst system using the boron-based cocatalyst, the molar ratio of the central metal to the boron atom is preferably 1:0.01-1:100, and more preferably, 1:0.5-1:5.

Meanwhile, a mixture of the boron compound and the organic aluminum compound or a mixture of the boron compound and the aluminoxane compound may be used, if necessary. In connection with this, the aluminum compound is used to remove polar compounds acting as a catalytic poison from a reaction solvent, and may act as an alkylating agent if X of the catalyst components is halogen.

The organic aluminum compound is expressed by the following Formula 10.

$$(R^{13})_rAl(E)_{3-r} \qquad \text{Formula 10}$$

In the above Formula, $R^{13}$ is a $C_1$-$C_8$ alkyl group, E is a hydrogen atom or a halogen atom, and r is an integer ranging from 1 to 3.

The organic aluminum compound is exemplified by trialkylaluminum including trimethylaluminum, triethylaluminum, tripropylaluminum, triisobutylaluminum, and trihexylaluminum; dialkylaluminum chloride including dimethylaluminum chloride, diethylaluminum chloride, dipropylaluminum chloride, diisobutylaluminum chloride, and dihexylaluminum chloride; alkylaluminum dichloride including methylaluminum dichloride, ethylaluminum dichloride, propylaluminum dichloride, isobutylaluminum dichloride, and hexylaluminum dichloride; or dialkylaluminum hydride including dimethylaluminum hydride, diethylaluminum hydride, dipropylaluminum hydride, diisobutylaluminum hydride, and dihexylaluminum hydride. Trialkylaluminum is preferable, and triethylaluminum and triisobutylaluminum are more preferable.

In connection with this, the molar ratio of the central metal: the boron atom:the aluminum atom is preferably 1:0.1-100: 10-1000, and more preferably, 1:0.5-5:25-500.

According to another aspect of the present invention, in a method of producing ethylene polymers using the transition metal catalyst system, the transition metal catalyst, the cocatalyst, and ethylene or a vinyl-based comonomer come into contact with each other in the presence of a predetermined organic solvent. At this stage, the transition metal catalyst and the cocatalyst are separately loaded into a reactor, or loaded into the reactor after they are previously mixed with each other. There are no limits to mixing conditions, such as the order of addition, temperature, or concentration.

The organic solvent useful in the method is $C_3$-$C_{20}$ hydrocarbons, and is exemplified by butane, isobutane, pentane, hexane, heptane, octane, isooctane, nonane, decane, dodecane, cyclohexane, methylcyclohexane, benzene, toluene, or xylene.

In detail, when the ethylene homopolymer, that is, high density polyethylene (HDPE), is produced, ethylene is used alone as a monomer, and pressure of ethylene useful to the present invention is 1-1000 atm, and preferably, 10-150 atm. Furthermore, a polymerization temperature is 80-300° C., and preferably, 120-250° C.

Additionally, when the copolymers of ethylene and α-olefins are produced, $C_3$-$C_{18}$ α-olefins are used as comonomers along with ethylene, and are selected from the group consisting of propylene, 1-butene, 1-pentene, 4-methyl-1-pentene, 1-hexene, 1-octene, 1-decene, 1-dodecene, 1-hexadecene, and 1-octadecene. More preferably, 1-butene, 1-hexene, 1-octene, or 1-decene is copolymerized with ethylene. In connection with this, the pressure of ethylene and the polymerization temperature are preferably the same as in the method of producing high density polyethylene. The ethylene copolymers produced according to the present invention include 60 wt % or more ethylene, and preferably, 75 wt % ethylene. As described above, linear low density polyethylene (LLDPE) which is produced using $C_4$-$C_{10}$ α-olefin as the comonomer has a density of 0.910-0.940 g/cc, and, in connection with this, it is possible to produce very or ultra low density polyethylene (VLDPE or ULDPE) having a density of 0.910 g/cc or less. As well, in the course of producing the ethylene homopolymer or copolymers according to the present invention, hydrogen may be used as a molecular weight controlling agent to control a molecular weight, and the ethylene homopolymer or copolymers typically has weight average molecular weight (Mw) of 80,000-500,000.

Since the catalyst system of the present invention is homogeneous in a polymerization reactor, it is preferable for application to a solution polymerization process which is conducted at a temperature of a melting point or higher of the polymer to be produced. However, as disclosed in U.S. Pat. No. 4,752,597, the transition metal catalyst and the cocatalyst may be supported by a porous metal oxide supporter so as to be used in a slurry polymerization process or a gaseous polymerization process as a heterogeneous catalyst system.

A better understanding of the present invention may be obtained through the following examples which are set forth to illustrate, but are not to be construed as the limit of the present invention.

Syntheses of all ligands and catalysts were conducted using standard Schlenk or globe box technology in a nitrogen atmosphere if not specifically described otherwise. The organic solvents used in the reactions were refluxed in the presence of sodium metal and benzophenone to remove moisture, and distilled immediately before they were used. $^1$H-NMR analyses of the produced ligands and catalysts were carried out at normal temperature using Varian Oxford 300 MHz.

n-heptane as a polymerization solvent was passed through a column in which a molecular sieve 5A and activated alumina were packed, and bubbling was conducted using highly pure nitrogen to sufficiently remove moisture, oxygen, and other catalytic poison materials before it was used. The resulting polymers were analyzed using the following methods.

1. Melt Index (MI)

Measurement was conducted based on ASTM D 2839.

2. Density

Measurement was conducted using a density gradient column based on ASTM D 1505.

3. Analysis of a Melting Point ($T_m$)

Measurement was conducted using Dupont DSC2910 in a nitrogen atmosphere at a rate of 10° C./min under a $2^{nd}$ heating condition.

4. Molecular Weight and Molecular Weight Distribution

Measurement was conducted using PL210 GPC which was equipped with PL Mixed-BX2+preCol in a 1,2,3-trichlorobenzene solvent at 135° C. and a rate of 1.0 mL/min, and the molecular weight was revised using a PL polystyrene standard material.

5. α-Olefin Content of Copolymer (Wt %)

Measurement was conducted using a Bruker DRX500 nuclear magnetic resonance spectroscope at 125 MHz in a mixed solvent of 1,2,4-trichlorobenzene/$C_6D_6$ (⅔ weight fraction) at 120° C. in a $^{13}$C-NMR mode (Bibliography: Randal, J. C. *JMS-Rev. Macromol. Chem. Phys.* 1980, C29, 201).

Preparation Example 1

Synthesis of
4-methyl-2,6-bis(2'-isopropylphenyl)phenol

A mixed solution of 1 mL of water and 4 mL of dimethoxyethane was added into a flask into which 2,6-dibromo-4-methylanisole (400 mg, 1.43 mmol), 2-isopropylphenylboronic acid (720 mg, 4.39 mmol), palladium acetate (14 mg, 0.062 mmol), triphenylphosphine (60 mg, 0.23 mmol), and potassium phosphate (940 mg, 4.43 mmol) were already added, and then refluxed at normal temperature for 6 hours. After cooling to normal temperature, an ammonium chloride aqueous solution (5 mL) and 10 mL of diethylether were added thereto to separate an organic layer and extract residues using diethylether. The separated organic layer was dried with magnesium sulfate and volatile materials were then removed to produce 670 mg of grey 4-methyl-2,6-bis(2'-isopropylphenyl)anisole solid. The anisole thus produced was dissolved in 5 mL of methylene chloride without separate purification, 3 mL of boron tribromide (1 M methylene chloride solution) was dropped thereon at −78° C., and a reaction was carried out while the temperature was slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 0.47 g of white 4-methyl-2,6-bis(2'-isopropylphenyl)phenol solid.

Yield: 95%, $^1$H-NMR (CDCl$_3$) δ=1.12-1.19 (m, 12H), 2.34 (s, 3H), 2.93 (m, 2H), 4.51 (s, 1H), 6.95 (s, 2H), 7.24 (d, 4H), 7.42 (t, 4H) ppm Synthesis of (dichloro)(pentamethylcyclopentadienyl)(4-methyl-2,6-bis(2'-isopropylphenyl)phenoxy)titanium(IV)

4-methyl-2,6-bis(2'-isopropylphenyl)phenol (344 mg, 1 mmol) and sodium hydride (72 mg, 3 mmol) were dissolved in 10 mL of toluene, and then refluxed for 4 hours. Subsequently, cooling to normal temperature was conducted, a solution in which (trichloro)(pentamethylcyclopentadienyl)titanium(IV) (289 mg, 1 mmol) was dissolved in 5 mL of toluene was slowly added thereto, and reflux was conducted for 24 hours. After the reaction was finished, volatile materials were removed, washing was conducted using purified hexane, recrystallization was conducted using a mixed solution of toluene/hexane at −35° C., filtration was conducted, and drying was conducted at reduced pressure to produce 352 mg of red solid component.

Yield: 67%, $^1$H-NMR (C$_6$D$_6$) δ=0.95-1.26 (m, 12H), 1.62 (s, 15H), 1.88 (s, 3H), 3.17 (m, 2H), 6.94-7.29 (m, 10H) ppm Example 1

300 mL of n-heptane was added into a stainless steel reactor which was purged with nitrogen after sufficient drying and had a volume of 500 mL, and 0.5 mL of triisobutylaluminum (Aldrich) (200 mM n-heptane solution) was added thereto. The temperature of the reactor was then increased to 140° C., and, subsequently, 0.2 mL of (dichloro)(pentamethylcyclopentadienyl)(4-methyl-2,6-bis(2'-isopropylphenyl)phenoxy)titanium(IV) (5 mM toluene solution), produced according to preparation example 1, and 0.3 mL of triphenylmethylinium tetrakis(pentafluorophenyl)borate (99%, Boulder Scientific) (5 mM toluene solution) were sequentially added thereto. Ethylene was then injected into the reactor until the pressure in the reactor was 30 atm, and was continuously fed for polymerization. 10 min after the reaction started, 10 mL of ethanol (including 10 vol % hydrochloric acid aqueous solution) were added to finish the polymerization, agitation was conducted for 4 hours along with 1500 mL of additional ethanol, and products were filtered and separated. The resulting product was dried in a vacuum oven at 60° C. for 8 hours to produce 7.3 g of polymer. The polymer had a melting point of 132.1° C. and a melt index of 0.001 g/10 min or less, and a weight average molecular weight of 393,000 and a molecular weight distribution of 3.36, which were determined through gel chromatography analysis.

Example 2

15 mL of 1-octene were injected into a reactor which was the same as in example 1, and polymerization was then conducted through the same procedure as in example 1 except that 0.3 mL of (dichloro)(pentamethylcyclopentadienyl)(4-methyl-2,6-bis(2'-isopropylphenyl)phenoxy)titanium(IV) (5 mM toluene solution) and 0.45 mL of triphenylmethylinium tetrakis(pentafluorophenyl)borate (Boulder Scientific) (5 mM toluene solution) were added after 0.75 mL of triisobutylaluminum (Aldrich) (200 mM n-heptane solution) were added. 4.0 g of dried polymer was obtained. The weight average molecular weight was 175,000 and a molecular weight distribution was 5.91, which were determined through gel chromatography analysis. The melt index was 0.12 g/10 min, the melting point of the polymer was 114.7° C., the density was 0.9215 g/cc, and the content of 1-octene was 7.8 wt %.

Preparation Example 2

Synthesis of 4-methyl-2-(2'-isopropylphenyl)phenol

A mixed solution of 1 mL of water and 4 mL of dimethoxyethane was added into a flask into which 2-bromo-4-methylanisole (600 mg, 2.98 mmol), 2-isopropylphenylboronic acid (734 mg, 4.47 mmol), palladium acetate (16 mg, 0.074 mmol), triphenylphosphine (72 mg, 0.27 mmol), and potassium phosphate (1.12 g, 5.28 mmol) were already added, and then refluxed at normal temperature for 6 hours. After cooling to normal temperature, an ammonium chloride aqueous solution (5 mL) and 10 mL of diethylether were added thereto to separate an organic layer and extract residues with diethylether. The separated organic layer was dried with magnesium sulfate and volatile materials were removed to produce 850 mg of grey 4-methyl-2-(2'-isopropylphenyl)anisole solid. The anisole thus produced was dissolved in 5 mL of methylene chloride without separate purification, 3 mL of boron tribromide (1 M methylene chloride solution) was dropped thereonto at −78° C., and a reaction was carried out while the temperature slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 633 mg of white 4-methyl-2,6-(2'-isopropylphenyl)phenol solid.

Yield: 93%, $^1$H-NMR (CDCl$_3$) δ=1.10-1.21 (q, 6H), 2.33 (s, 3H), 2.91 (m, 1H), 4.63 (s, 1H), 6.87-7.51 (m, 7H) ppm Synthesis of (dichloro)(pentamethylcyclopentadienyl)(4-methyl-2-(2'-isopropylphenyl)phenoxy)titanium(IV)

4-methyl-2-(2'-isopropylphenyl)phenol (1 g, 4.41 mmol) and sodium hydride (318 mg, 13.25 mmol) were dissolved in 10 mL of toluene, and then refluxed for 4 hours. Subsequently, cooling to normal temperature was conducted, a solution in which (trichloro)(pentamethylcyclopentadienyl)titanium(IV) (1.15 g, 4.0 mmol) was dissolved in 5 mL of toluene was slowly dropped thereonto, and reflux was conducted for 24 hours. After the reaction was finished, volatile materials were removed, washing was conducted using purified hexane, recrystallization was conducted using a mixed solution of toluene/hexane at −35° C., filtration was conducted, and drying was conducted at reduced pressure to produce 1.53 g of red solid component.

Yield: 67%, $^1$H-NMR (C$_6$D$_6$) δ=0.96-1.07 (m, 6H), 1.76 (s, 15H), 1.89 (s, 3H), 2.99 (m, 1H), 6.85-7.37 (m, 7H) ppm Example 3

Polymerization was conducted through the same procedure as in example 2 except that 0.2 mL of (dichloro)(pentamethylcyclopentadienyl)(4-methyl-2-(2'-isopropylphenyl)phenoxy)titanium(IV) (5 mM toluene solution) produced according to preparation example 2 were used. The product was dried to produce 5.5 g of polymer. The polymer had a melting point of 132.1° C. and a melt index of 0.06 g/10 min, and a weight average molecular weight of 188,000 and a molecular weight distribution of 4.30 which were determined through gel chromatography analysis.

Preparation Example 3

Synthesis of 4-methyl-2,6-diphenylphenol

A mixed solution of 1 mL of water and 4 mL of dimethoxyethane was added into a flask into which 2,6-dibromo-4-methylanisole (400 mg, 1.43 mmol), phenylboronic acid (535 mg, 4.39 mmol), palladium acetate (14 mg, 0.062 mmol), triphenylphosphine (60 mg, 0.23 mmol), and potassium phosphate (940 mg, 4.43 mmol) were already added, and then refluxed at normal temperature for 6 hours. After cooling to normal temperature, an ammonium chloride aqueous solution (5 mL) and 10 mL of diethylether were added thereto to separate an organic layer and extract residues using diethylether. The separated organic layer was dried with magnesium sulfate and volatile materials were removed to produce 420 mg of grey 4-methyl-2,6-diphenylanisole solid. The anisole thus produced was dissolved in 5 mL of methylene chloride without separate purification, 3 mL of boron tribromide (1 M methylene chloride solution) were dropped thereonto at −78° C., and the reaction was carried out while the temperature was slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 333 mg of white 4-methyl-2,6-diphenylphenol solid.

Yield: 89%, $^1$H-NMR (CDCl$_3$) δ=2.36 (s, 3H), 5.24 (s, 1H), 7.01 (s, 2H), 7.37 (t, 2H), 7.47 (t, 4H), 7.54 (d, 4H) ppm Synthesis of (dichloro)(pentamethylcyclopentadienyl)(4-methyl-2,6-diphenylphenoxy)titanium(IV)

4-methyl-2,6-diphenylphenol (400 mg, 1.53 mmol) and sodium hydride (110 mg, 4.60 mmol) were dissolved in 10 mL of toluene, and then refluxed for 4 hours. Subsequently, cooling to normal temperature was conducted, a solution in which (trichloro)(pentamethylcyclopentadienyl)titanium(IV) (376 mg, 1.30 mmol) was dissolved in 5 mL of toluene was slowly dropped thereonto, and reflux was conducted for 24 hours. After the reaction finished, volatile materials were removed, washing was conducted using purified hexane, recrystallization was conducted using a mixed solution of toluene/hexane at −35° C., filtration was conducted, and drying was conducted at reduced pressure to produce 308 mg of red solid component.

Yield: 46%, $^1$H-NMR ($C_6D_6$) δ=1.87 (s, 3H), 1.67 (s, 15H), 6.97-7.18 (m, 12H) ppm

Example 4

Polymerization was conducted through the same procedure as in example 2 except that 0.2 mL of (dichloro)(pentamethylcyclopentadienyl)(4-methyl-2,6-diphenylphenoxy)titanium(IV) (5 mM toluene solution) produced according to preparation example 3 were used. The product was dried to produce 5.8 g of polymer. The polymer had a melting point of 131.4° C. and a melt index of 0.011 g/10 min, and a weight average molecular weight of 349,000 and a molecular weight distribution of 2.74, which were determined through gel chromatography analysis.

Preparation Example 4

Synthesis of (dichloro)(pentamethylcyclopentadienyl)(2-phenylphenoxy)titanium(IV)

After 0.86 g of 2-phenylphenol (5.07 mmol) (Aldrich, 99%) were dissolved in 40 mL of toluene, 2.4 mL of butyl lithium (2.5 M hexane solution) were slowly dropped thereonto at 0° C. After the reaction was conducted at normal temperature for 12 hours, a solution in which (trichloro)(pentamethylcyclopentadienyl)titanium(IV) (1.32 g, 4.56 mmol) was dissolved in 10 mL of toluene was slowly dropped thereonto at 0° C. After agitation was conducted at normal temperature for 12 hours, filtration was conducted, volatile materials were removed, and recrystallization was conducted using a mixed solution of toluene/hexane at −35° C. to produce 1.64 g of an orange-colored solid component.

Yield: 85%; $^1$H-NMR ($C_6D_6$) δ=1.68 (s, 15H), 6.82-7.26 (m, 9H) ppm

Example 5

Polymerization was conducted through the same procedure as in example 2 except that 0.2 mL of (dichloro)(pentamethylcyclopentadienyl)(2-phenylphenoxy)titanium(IV) (5 mM toluene solution) produced according to preparation example 4 were used. The product was dried to produce 10.5 g of polymer. The polymer had a melting point of 130.3° C. and a melt index of 0.001 g/10 min or less, and a weight average molecular weight of 303,000 and a molecular weight distribution of 3.4, which were determined through gel chromatography analysis.

Example 6

Polymerization was conducted through the same procedure as in example 2 except that 0.3 mL of (dichloro)(pentamethylcyclopentadienyl)(2-phenylphenoxy)titanium(IV) (5 mM toluene solution) produced according to preparation example 4 were used. 7.8 g of dried polymer were obtained. The weight average molecular weight was 139,000 and the molecular weight distribution was 2.5, as determined through gel chromatography analysis. The melt index was 0.2 g/10 min, the melting point was 118.7° C., the density was 0.9197 g/cc, and the content of 1-octene was 4.5 wt %.

Preparation Example 5

Synthesis of 2-isopropyl-6-phenylphenol

A mixed solution of 8 mL of water and 32 mL of dimethoxyethane was added into a flask into which 2-bromo-6-isopropylanisole (1.98 g, 8.64 mmol), phenylboronic acid (2.10 g, 17.28 mmol), palladium acetate (96 mg, 0.43 mmol), triphenylphosphine (0.225 g, 0.86 mmol), and potassium phosphate (11 g, 51.84 mmol) were already added, and then refluxed at normal temperature for 12 hours. After cooling to normal temperature, an ammonium chloride aqueous solution (15 mL) and 30 mL of diethylether were added thereto to separate an organic layer and extract residues using diethylether. The separated organic layer was dried with magnesium sulfate and volatile materials were removed to produce 2 g of grey 2-isopropyl-6-phenylanisole solid. The anisole thus produced was dissolved in 15 mL of methylene chloride without separate purification, 12 mL of boron tribromide (1 M methylene chloride solution) were dropped thereonto at −78° C., and the reaction was carried out for 12 hours while the temperature was slowly increased to normal temperature. After the reaction, a mixed solution of water (15 mL) and diethylether (30 mL) was added to separate an organic layer and extract an aqueous solution layer using diethylether (15 mL×3), and the separated organic layer was dried. Residues from which volatile components were removed at reduced pressure were purified using a silica gel chromatography tube in a mixed solvent of hexane and methylene chloride to produce 1.72 g of white 2-isopropyl-6-phenylphenol solid.

Yield: 94%, $^1$H-NMR ($CDCl_3$) δ=1.307 (d, 6H), 3.45 (m, 1H), 5.09 (s, 1H), 6.95-7.43 (m, 8H) ppm

Synthesis of (dichloro)(pentamethylcyclopentadienyl (2-isopropyl-6-phenylphenoxy)titanium(IV)

2-isopropyl-6-phenylphenol (700 mg, 3.28 mmol) and sodium hydride (236 mg, 9.84 mmol) were dissolved in 10 mL of toluene, and then refluxed for 4 hours. Subsequently, cooling to normal temperature was conducted, a solution in which (trichloro)(pentamethylcyclopentadienyl)titanium (IV) (930 mg, 3.21 mmol) was dissolved in 5 mL of toluene was slowly dropped thereonto, and reflux was conducted for 24 hours. After the reaction was finished, volatile materials were removed, washing was conducted using purified hexane, recrystallization was conducted using a mixed solution of toluene/hexane at −35° C., filtration was conducted, and drying was conducted at reduced pressure to produce 1.0 g of red solid component.

Yield: 64%, $^1$H-NMR ($C_6D_6$) δ=1.324 (d, 6H), 1.63 (s, 15H), 3.53 (m, 1H), 7.05-7.66 (m, 8H) ppm

Example 7

Polymerization was conducted through the same procedure as in example 2 except that 0.2 mL of (dichloro)(pentamethylcyclopentadienyl)(2-isopropyl-6-phenylphenoxy)titanium(IV) (5 mM toluene solution) produced according to preparation example 5 were used. The product was dried to produce 5.5 g of polymer. The polymer had a melting point of 132.6° C. and a melt index of 0.002 g/10 min, and a weight average molecular weight of 390,000 and a molecular weight distribution of 4.08, as determined through gel chromatography analysis.

Preparation Example 6

Synthesis of 4-methyl-2,6-bis(3',5'-dimethylphenyl)phenol

A mixed solution of 1 mL of water and 4 mL of dimethoxyethane was added into a flask into which 2,6-dibromo-4-methylanisole (400 mg, 1.43 mmol), 3,5-dimethylphenylboronic acid (658 mg, 4.39 mmol), palladium acetate (14 mg, 0.062 mmol), triphenylphosphine (60 mg, 0.23 mmol), and potassium phosphate (940 mg, 4.43 mmol) were already added, and then refluxed at normal temperature for 6 hours. After cooling to normal temperature, an ammonium chloride aqueous solution (5 mL) and 10 mL of diethylether were added thereto to separate an organic layer and extract residues using diethylether. The separated organic layer was dried with magnesium sulfate and volatile materials were removed to produce 453 mg of white 4-methyl-2,6-bis(3',5'-dimethylphenyl)anisole solid (yield 96%). The anisole thus produced was dissolved in 5 mL of methylene chloride without separate purification, 3 mL of boron tribromide (1 M methylene chloride solution) were dropped thereonto at −78° C., and the reaction was carried out while the temperature was slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 0.41 g of white 4-methyl-2,6-bis(3',5'-dimethylphenyl)phenol solid.

Yield: 92%, $^1$H-NMR (CDCl$_3$) δ=1.55 (s, 3H), 2.37 (s, 12H), 5.35 (s, 1H), 7.05 (s, 2H), 7.15 (s, 4H), 7.27 (4, 2H) ppm

Preparation Example 7

Synthesis of 4-methyl-2,6-bis(biphenyl)phenol

A mixed solution of 1 mL of water and 4 mL of dimethoxyethane was added into a flask into which 2,6-dibromo-4-methylanisole (400 mg, 1.43 mmol), biphenylboronic acid (870 mg, 4.39 mmol), palladium acetate (14 mg, 0.062 mmol), triphenylphosphine (60 mg, 0.23 mmol), and potassium phosphate (940 mg, 4.43 mmol) were already added, and then refluxed at normal temperature for 6 hours. After cooling to normal temperature, an ammonium chloride aqueous solution (5 mL) and 10 mL of diethylether were added thereto to separate an organic layer and extract residues using diethylether. The separated organic layer was dried with magnesium sulfate and volatile materials were removed to produce 560 mg of white 4-methyl-2,6-bis(biphenyl)anisole solid (yield 95%). The anisole thus produced was dissolved in 5 mL of methylene chloride without separate purification, 3 mL of boron tribromide (1 M methylene chloride solution) were dropped thereonto at −78° C., and the reaction was carried out while the temperature was slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 540 mg of white 4-methyl-2,6-bis(biphenyl)phenol solid.

Yield: 92%, $^1$H-NMR (CDCl$_3$) δ=2.39 (s, 3H), 5.34 (s, 1H), 7.16-7.72 (m, 20H) ppm Synthesis of (dichloro)(pentamethylcyclopentadienyl)(4-methyl-2,6-bis(biphenyl)phenoxy)titanium(IV)

4-methyl-2,6-bis(biphenyl)phenol (206 mg, 0.5 mmol) and sodium hydride (36 mg, 1.5 mmol) were dissolved in 10 mL of toluene, and then refluxed for 1 hour. Subsequently, cooling to normal temperature was conducted, a solution in which (trichloro)(pentamethylcyclopentadienyl)titanium(IV) (130 mg, 0.45 mmol) was dissolved in 10 mL of toluene was slowly dropped thereonto, and reflux was conducted for 24 hours. After the reaction was finished, volatile materials were removed, washing was conducted using purified hexane, recrystallization was conducted using a mixed solution of toluene/hexane at −35° C., filtration was conducted, and drying was conducted at reduced pressure to produce 0.12 g of yellow solid component.

Yield: 42%, $^1$H-NMR (CDCl$_3$) δ=1.60 (s, 15H), 2.48 (s, 3H), 7.08-8.15 (m, 20H) ppm

Preparation Example 8

Synthesis of 4-methyl-2,6-bis(1'-naphthyl)phenol

A mixed solution of 1 mL of water and 4 mL of dimethoxyethane was added into a flask into which 2,6-dibromo-4-methylanisole (700 mg, 2.63 mmol), 1-naphthylboronic acid (1.39 g, 8.07 mmol), palladium acetate (25 mg, 0.12 mmol), triphenylphosphine (94 mg, 0.35 mmol), and potassium phosphate (1.9 g, 8.9 mmol) were already added, and then refluxed at normal temperature for 6 hours. After cooling to normal temperature, an ammonium chloride aqueous solution (5 mL) and 10 mL of diethylether were added thereto to separate an organic layer and extract residues using diethylether. The separated organic layer was dried with magnesium sulfate and volatile materials were removed to produce 880 mg of grey 4-methyl-2,6-bis(1'-naphthyl)anisole solid (yield 89%). The anisole thus produced was dissolved in 10 mL of methylene chloride without separate purification, 5 mL of boron tribromide (1 M methylene chloride solution) were dropped thereonto at −78° C., and the reaction was carried out while the temperature was slowly increased to normal temperature. After the reaction, a mixed solution of water (5 mL) and diethylether (10 mL) was added to separate an organic layer and extract an aqueous solution layer using diethylether (5 mL×3), and the separated organic layer was dried. Residues from which volatile components were removed at reduced pressure were purified using a silica gel chromatography tube in a mixed solvent of hexane and methylene chloride to produce 805 mg of white 4-methyl-2,6-bis(1'-naphthyl)phenol solid.

Yield: 85%, $^1$H-NMR (CDCl$_3$) δ=2.41 (s, 3H), 4.71 (s, 1H), 7.21-7.92 (m, 16H) ppm

Comparative Preparation Example 1

Synthesis of (dichloro)(pentamethylcyclopentadienyl)(2,6-di-tert-butylphenoxy)titanium(IV)

After 600 mg of 2,6-di-tert-butylphenol (2.91 mmol) (Aldrich, 99%) were dissolved in 30 mL of diethylether, 1.28 mL of butyl lithium (2.5 M hexane solution) were slowly dropped thereonto at −31° C. After 1 hour, agitation was conducted at normal temperature for 6 hours. The resulting mixture was dissolved in diethylether, and a solution in which (trichloro)(pentamethylcyclopentadienyl)titanium(IV) (752 mg, 2.60 mmol) was dissolved in 10 mL of diethylether was slowly dropped thereonto at −30° C. After 1 hour, agitation was conducted at normal temperature for 6 hours. The solvent was removed from the resulting product, and the solvent-free product was dissolved in 10 mL of toluene and then recrystallized to produce 829 mg of red solid component.

Yield: 69%; 1H-NMR (CDCl$_3$) δ=1.37 (s, 18H), 2.10 (s, 15H), 6.50-7.20 (m, 3H) ppm Comparative Example 1

Polymerization was conducted through the same procedure as in example 1 except that 0.2 mL of (dichloro)(pentamethylcyclopentadienyl)(2,6-di-tert-butylphenoxy)titanium(IV) (5 mM toluene solution) produced according to comparative preparation example 1 were used. The product was dried to produce 1.4 g of polymer. The polymer had a melting point of 133.1° C. and a melt index of 0.25 g/10 min, and a weight average molecular weight of 182,000 and a molecular weight distribution of 5.76, which were determined through gel chromatography analysis.

Comparative Example 2

Polymerization was conducted through the same procedure as in example 2 except that 0.2 mL of (trimethyl)(pentamethylcyclopentadienyl)titanium(IV) (97%, Strem) (5 mM toluene solution), 0.24 mL of triisobutylaluminum (200 mM n-heptane solution) (Aldrich), and 0.25 mL of triphenylmethylinium tetrakis(pentafluorophenyl)borate (99%, Boulder Scientific) (5 mM toluene solution) were used. The product was dried to produce 3.0 g of polymer. The polymer had a melting point of 132.0° C. and a melt index of 0.16 g/10 min, and a weight average molecular weight of 150,000 and a molecular weight distribution of 5.47, which were determined through gel chromatography analysis.

Comparative Example 3

Polymerization was conducted through the same procedure as in example 3 except that 0.4 mL of (trimethyl)(pentamethylcyclopentadienyl)titanium(IV) (97%, Strem) (5 mM toluene solution), 1.0 mL of triisobutylaluminum (200 mM n-heptane solution) (Aldrich), and 0.6 mL of triphenylmethylinium tetrakis(pentafluorophenyl)borate (99%, Boulder Scientific) (5 mM toluene solution) were used. 1.1 g of dried polymer were produced.

Comparative Example 4

Polymerization was conducted through the same procedure as in example 1 except that 0.2 mL of rac-dimethylsilyl-bis(2-methylindenyl)zirconium dichloride (Boulder Scientific) (5 mM toluene solution) were used as a catalyst component. The product was dried to produce 25.0 g of polymer. The polymer had a melting point of 132.5° C. and a melt index of 4.4 g/10 min, and a weight average molecular weight of 59,000 and a molecular weight distribution of 8.9, which were determined through gel chromatography analysis.

Comparative Example 5

Polymerization was conducted through the same procedure as in example 3 except that 0.3 mL of rac-dimethylsilyl-bis(2-methylindenyl)zirconium dichloride (Boulder Scientific) (5 mM toluene solution) were used as a catalyst component. The product was dried to produce 15.0 g of polymer. The polymer had a melting point of 123.2° C. and a melt index of 110 g/10 min, and a weight average molecular weight of 28,000 and a molecular weight distribution of 12.0, which were determined through gel chromatography analysis. The 1-octene content of the polymer was 2.4 wt %.

The arylphenoxy catalyst system according to the present invention is advantageous in that it is easy to handle, it is possible to produce it using environmentally-friendly raw materials at high yield, and it has high catalytic activity in a high temperature solution polymerization condition due to its excellent thermal stability in the course of producing a polymer having a high molecular weight, thus it is more useful than a conventional non-metallocene single-site catalyst. Therefore, it is useful for producing an ethylene homopolymer or copolymers of ethylene and α-olefins having various physical properties.

What is claimed is:

1. An arylphenoxy-based transition metal catalyst of Formula 1, which includes a cyclopentadienyl group and an arylphenoxide group as fixed ligands bound to a transition metal, wherein the ligands are not crosslinked to each other:

Formula 1

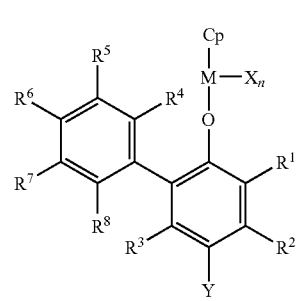

wherein M is a group IV transition metal of the periodic table;

Cp is a cyclopentadienyl group forming an $\eta^5$-bond with the transition metal, or a derivative thereof;

$R^1$, $R^2$, $R^3$, $R^4$, $R^5$, $R^6$, $R^7$, and $R^8$ are independently a hydrogen atom, a halogen atom, a $C_1$-$C_{20}$ linear or nonlinear alkyl group optionally substituted with one or more halogen atoms, a silyl group which contains the $C_1$-$C_{20}$ linear or nonlinear alkyl group optionally substituted with one or more halogen atoms, a $C_6$-$C_{30}$ aryl group optionally substituted with one or more halogen atoms, a $C_7$-$C_{30}$ arylalkyl group optionally substituted with one or more halogen atoms, a $C_1$-$C_{20}$ alkylalkoxy group optionally substituted with one or more halogen atoms, a $C_3$-$C_{20}$ alkyl-substituted siloxy group, or a $C_6$-$C_{20}$ aryl-substituted siloxy group, optionally with the proviso that substituent groups may be optionally bonded to form rings;

each X is independently selected from a halogen atom, a $C_1$-$C_{20}$ alkyl group, a $C_7$-$C_{30}$ arylalkyl group, an alkoxy group containing the $C_1$-$C_{20}$ alkyl group, a $C_3$-$C_{20}$ alkyl-substituted siloxy group, or an amido group having a $C_1$-$C_{20}$ hydrocarbon group;

Y is a hydrogen atom, a halogen atom, a $C_1$-$C_{20}$ linear or nonlinear alkyl group optionally substituted with one or more halogen atoms, a silyl group containing a $C_1$-$C_{20}$ linear or nonlinear alkyl group optionally substituted with one or more halogen atoms, a $C_6$-$C_{30}$ aryl group optionally substituted with one or more halogen atoms, a $C_7$-$C_{30}$ arylalkyl group optionally substituted with one or more halogen atoms, a $C_1$-$C_{20}$ alkylalkoxy group optionally substituted with one or more halogen atoms, a $C_3$-$C_{20}$ alkyl substituted siloxy group, a $C_6$-$C_{20}$ aryl-substituted siloxy group, an amido group or a phosphido group which has a $C_1$-$C_{20}$ hydrocarbon group, or a $C_1$-$C_{20}$ alkyl-substituted mercapto or nitro group; and n is 1 or 2 depending on the oxidation state of the transition metal.

2. The arylphenoxy-based transition metal catalyst as set forth in claim 1, wherein M is titanium, zirconium, or hafnium.

3. The arylphenoxy-based transition metal catalyst as set forth in claim 1, wherein Cp is cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, or isopropylfluorenyl.

4. The arylphenoxy-based transition metal catalyst as set forth in claim 1, wherein $R^1$, $R^2$, $R^3$, $R^4$, $R^5$, $R^6$, $R^7$, and $R^8$ are independently selected from a hydrogen atom, a halogen atom, a methyl group, an ethyl group, an isopropyl group, a tert-butyl group, an amyl group, a trimethylsilyl group, a tert-butyldimethylsilyl group, a triphenylsilyl group, a phenyl group, a naphthyl group, a biphenyl group, a 2-isopropylphenyl group, a 3,5-xylyl group, a 2,4,6-trimethylphenyl group, a benzyl group, a methoxy group, an ethoxy group, an isopropoxy group, a tert-butoxy group, a trimethylsiloxy group, a tert-butyldimethylsiloxy group, a triphenylsiloxy group, a trifluoromethyl group, or a pentafluorophenyl group.

5. The arylphenoxy-based transition metal catalyst as set forth in claim 1, wherein X is one or more of a halogen atom, a methyl group, an ethyl group, an isopropyl group, a tert-butyl group, an amyl group, a benzyl group, a methoxy group, an ethoxy group, an isopropoxy group, a tert-butoxy group, a trimethylsiloxy group, a tert-butyldimethylsiloxy group, a dimethylamino group, or a diethylamino group.

6. The arylphenoxy-based transition metal catalyst as set forth in claim 1, wherein Y is a hydrogen atom, a halogen atom, a methyl group, an ethyl group, an isopropyl group, a tert-butyl group, an amyl group, a trimethylsilyl group, a tert-butyldimethylsilyl group, a triphenylsilyl group, a phenyl group, a naphthyl group, a biphenyl group, a 2-isopropylphenyl group, a 3,5-xylyl group, a 2,4,6-trimethylphenyl group, a benzyl group, a methoxy group, an ethoxy group, an isopropoxy group, a tert-butoxy group, a trimethylsiloxy group, a dimethylsiloxy group, a triphenylsiloxy group, a trifluoromethyl group, a pentafluorophenyl group, a dimethylamino group, a diethylamino group, an ethylmercaptan group, an isopropylmercaptan group, or a nitro group.

7. A method of producing an ethylene homopolymer or a copolymer of ethylene and an α-olefin comprising the step of reacting ethylene alone or in admixture with an α-olefin in the presence of the arylphenoxy-based transition metal catalyst of claim 1 at 10-150 atm and a reaction temperature of 120-250° C.

* * * * *